(12) United States Patent
Hill, Jr. et al.

(10) Patent No.: US 7,071,465 B2
(45) Date of Patent: Jul. 4, 2006

(54) ION MOBILITY SPECTROMETRY METHOD AND APPARATUS

(75) Inventors: Herbert Henderson Hill, Jr., Pullman, WA (US); Maggie Tam, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 10/966,325

(22) Filed: Oct. 14, 2004

(65) Prior Publication Data

US 2005/0109930 A1    May 26, 2005

Related U.S. Application Data

(60) Provisional application No. 60/511,173, filed on Oct. 14, 2003.

(51) Int. Cl.
*H01J 49/00* (2006.01)
*H01J 49/10* (2006.01)

(52) U.S. Cl. ............... 250/286; 250/281; 250/282; 250/288

(58) Field of Classification Search .................. None
See application file for complete search history.

(56) References Cited

U.S. PATENT DOCUMENTS

| | | | | |
|---|---|---|---|---|
| 4,633,083 A * | 12/1986 | Knorr et al. | ............... | 250/282 |
| 4,839,143 A * | 6/1989 | Vora et al. | ............... | 422/98 |
| 4,855,595 A * | 8/1989 | Blanchard | ............... | 250/287 |
| 5,053,343 A * | 10/1991 | Vora et al. | ............... | 436/153 |
| 5,400,614 A * | 3/1995 | Feola | ............... | 62/233 |
| 5,405,781 A * | 4/1995 | Davies et al. | ............... | 436/52 |
| 5,491,337 A * | 2/1996 | Jenkins et al. | ............... | 250/287 |
| 5,552,600 A * | 9/1996 | Davies et al. | ............... | 250/286 |
| 5,838,002 A * | 11/1998 | Sheehan | ............... | 250/288 |
| 6,011,258 A * | 1/2000 | Baumbach et al. | ............... | 250/286 |
| 6,124,592 A * | 9/2000 | Spangler | ............... | 250/287 |
| 6,278,111 B1 * | 8/2001 | Sheehan et al. | ............... | 250/288 |
| 6,291,821 B1 * | 9/2001 | Danylewych-May et al. | ............... | 250/286 |
| 6,459,079 B1 * | 10/2002 | Machlinski et al. | ............... | 250/286 |
| 6,627,878 B1 * | 9/2003 | Machlinski et al. | ............... | 250/287 |
| 6,630,663 B1 * | 10/2003 | Murphy et al. | ............... | 250/286 |
| 6,690,005 B1 | 2/2004 | Jenkins et al. | | |
| 6,727,495 B1 * | 4/2004 | Li | ............... | 250/286 |
| 6,740,874 B1 * | 5/2004 | Doring | ............... | 250/287 |

(Continued)

OTHER PUBLICATIONS

Arbor Scientific: "Exploring Matter Activities", <http://www.arborsci.com/CoolStuff/cool16.htm>.*

(Continued)

*Primary Examiner*—Nikita Wells
*Assistant Examiner*—Bernard E. Souw
(74) *Attorney, Agent, or Firm*—Wells St. John P.S.

(57) ABSTRACT

The invention includes an ion mobility spectrometer having a liquid filled drift chamber. The chamber has an ionization region partitioned from and an ion separation region by a reversible ion-migration block. An electrical field within the chamber allows ions to migrate toward the electrode collector. Passage of ions from the ionization region is triggered by reversing the block allowing ions to migrate into the ion separation region. The invention includes a method of ion mobility analysis in liquid phase. Ions are mobilized to migrate through a drift liquid and are detected at an end of a drift chamber. The invention also includes a method of generating ions in a sample. A sample containing molecules in a first solvent is introduced into a second solvent through a charged capillary where the electrically charged sample is electro-disperses to ionize the molecules.

37 Claims, 9 Drawing Sheets

U.S. PATENT DOCUMENTS

| | | |
|---|---|---|
| 6,784,424 B1 | 8/2004 | Willoughby et al. |
| 6,797,943 B1 | 9/2004 | Losch et al. |
| 2005/0056775 A1* | 3/2005 | Cody et al. ................ 250/281 |
| 2005/0109930 A1* | 5/2005 | Hill et al. ................... 250/286 |

OTHER PUBLICATIONS

"Disappearing Cup", <http://www.elmhurst.edu/~chm/demos/DisappearingCup.html>.*

* cited by examiner

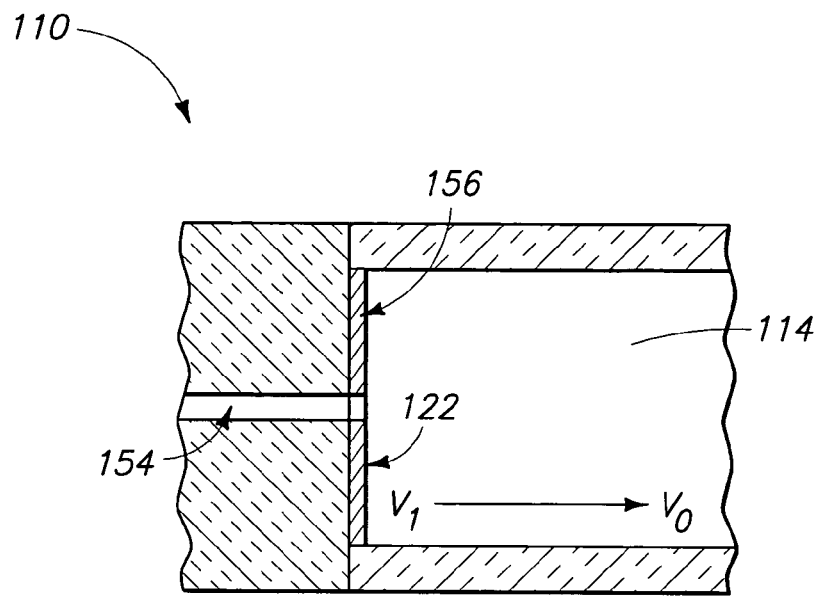
_FIG. 2_
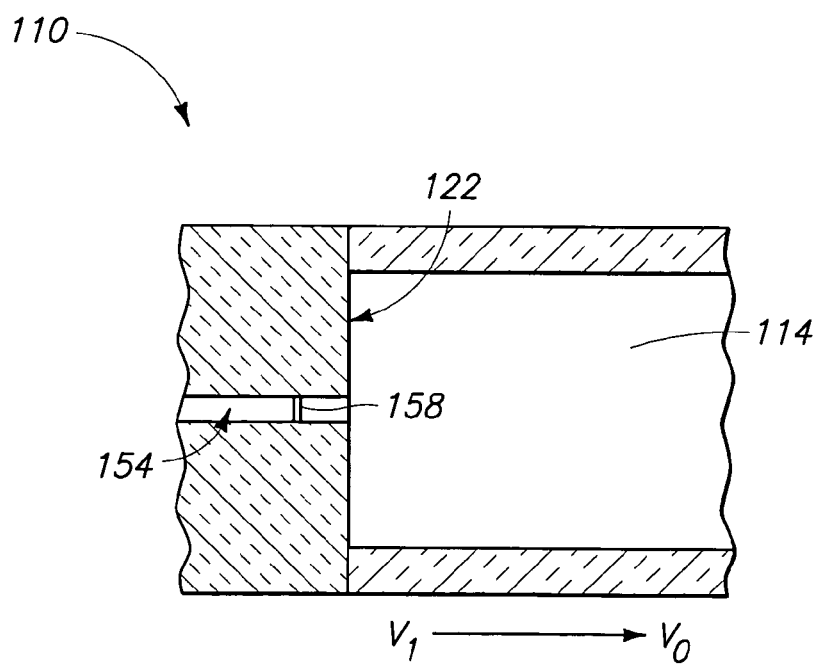
_FIG. 3_

ION MOBILITY SPECTROMETRY METHOD AND APPARATUS

RELATED PATENT DATA

This patent claims benefit of priority under 35 U.S.C. §119 to U.S. Provisional Patent Ser. No. 60/511,173, which was filed Oct. 14, 2003.

This invention was developed in part with Government support under contract DAAD190216350, awarded by the U.S. Army Research Office. The Government has certain rights in this invention.

TECHNICAL FIELD

The invention pertains to ion mobility spectroscopy systems, an ion mobility spectrometer, methods of conducting ion mobility analysis and methods of generating ions in a sample.

BACKGROUND OF THE INVENTION

A variety of analytical separation methods have been developed for differentiating between component molecules in a sample. Such methodology includes both gas-phase and liquid-phase chromatographic separations. Liquid-phase separation techniques include, for example, high performance liquid chromatography (HPLC), and capillary electrophoresis techniques such as capillary zone electrophoresis (CZE). Conventional gas-phase separation techniques include gas chromatography (GC) and ion mobility spectrometry (IMS). A comparison of typical resolution powers and efficiencies of these techniques indicates that gas-phase IMS can generally provide a greater efficiency relative to the alternative methods. However, although conventional IMS typically provides greater resolution than HPLC, the CZE and GC techniques can have a greater resolving power relative to IMS in the gas-phase.

In general an increase in resolving power for chromatographic methods is achieved by providing an increase in column length. For electrophoresis, an increase in resolving power can be achieved by providing an increase in applied voltage across the separation region. However, due to electrolytes utilized in the electrophoresis mobile phase, as the voltage is increased across a given channel length, the current increase heats the solution and can degrade resolving power. This heating effect can be a limiting factor on resolving power and miniaturization of capillary electrophoretic techniques.

Utilizing gas-phase IMS, which separates ions rather than neutral molecules, an increase in applied voltage across the drift field can be utilized to increase the resolving power in some instances. The general diffusion limited equation which relates ion mobility resolving power to operational parameters applies to both electrophoresis and IMS. Such equation is set forth below.

$$R^2 = \frac{1}{16\ln 2k}\frac{qV}{T} \Rightarrow R \propto \sqrt{\frac{qV}{T}}$$

As demonstrated by the equation (where k is Boltzmann's constant), the IMS resolving power R is directly proportional to the square root of the charge on the ion q and the total voltage across the drift region V, and inversely proportional to the square root of the drift gas temperature T. In gas-phase IMS, higher voltages across the drift tube can lead to more rapidly eluting ions and the resolving power becomes limited with the pulse width of ions through the ion gate. Thus, in order to maintain resolving power, drift length is typically increased as the voltage is increased. Since it can be desirable to use small sensors for ion mobility separation, the effect is particularly notable in these applications.

The ability to use a decreased sensor size is typically dependent upon utilization of a relatively low voltage differential across the drift tube. As indicated, the decrease in voltage differential can sacrifice resolving power of the instrument. Attempts to scale down device size for gas phase IMS have typically resulted in decreased resolving power and decreased signal to noise ratios. Such factors can thereby limit the ability to produce a small size gas-phase IMS device having sufficient resolving power to accurately analyze many types of compounds and substances. Accordingly, it is desirable to develop alternative ion mobility technology.

SUMMARY OF THE INVENTION

In one aspect, the invention encompasses an ion mobility spectrometer having a housing and a chamber containing a liquid within the housing. The chamber has a first end and an opposing second end with a central axis extending from the first end to the second end. The chamber has a first region which is gatedly electrically partitioned from a second region by an ion gate and/or an electric potential well. A plurality of ring electrodes are positioned within the housing and are configured to provide an electrostatic field along at least a portion of the central axis of the chamber.

In one aspect the invention includes an ion mobility analysis system which includes a device housing and an internal chamber. The chamber has an ionization region and an ion separation region, and has a longitudinal axis of the chamber passing centrally through both the ionizing region and the ion separation region. A series of annular electrodes are provided within the chamber. At least some of the electrodes in the series are aligned substantially parallel relative to each other and substantially normal relative to the longitudinal axis. A sample inlet is provided at a first end of the device and an ion collector is positioned within the chamber proximate a second end of the device. An ionization source is associated with the ionization region. The chamber contains a liquid and the device is configured to provide an electrical field within the chamber such that ions present in the chamber migrate through the liquid toward the electrode collector.

A reversible ion-migration block defines an interface between the ionization region and the ion separation region. The ion-migration block is configured to block passage of ions from the ionization region to the ion separation region until an occurrence of a triggering event which reverses the block allowing ions to migrate from the ionization region into the ion separation region.

In another aspect the invention encompasses a method of conducting ion mobility analysis. A drift chamber is provided which contains a drift fluid which can be a liquid, a supercritical fluid, or a pressurized gas. A sample is introduced into a first end of the chamber. Ions within the sample are mobilized to migrate through the drift fluid and are detected at a second end of the drift chamber.

In another aspect the invention encompasses a method of generating ions in a sample. A sample containing molecules in a first solvent is introduced into a second solvent in which the first solvent is partially soluble. To introduce the sample, the sample is passed through a charged capillary or other charged component such that electrically charged sample enters the second solvent where the sample electro-disperses to produce ions from the molecules, the ions being at least partially de-solvated with respect to the first solvent.

BRIEF DESCRIPTION OF THE DRAWINGS

Preferred embodiments of the invention are described below with reference to the following accompanying drawings.

FIG. 2. is a cross-sectional view of an ionization source in accordance with one aspect of the invention.

FIG. 3 is a cross-sectional view of an alternative ionization source in accordance with the invention.

FIG. 8 shows a liquid-phase ion mobility spectrum of $Na^+$.

DETAILED DESCRIPTION OF THE PREFERRED EMBODIMENTS

Figure 1:
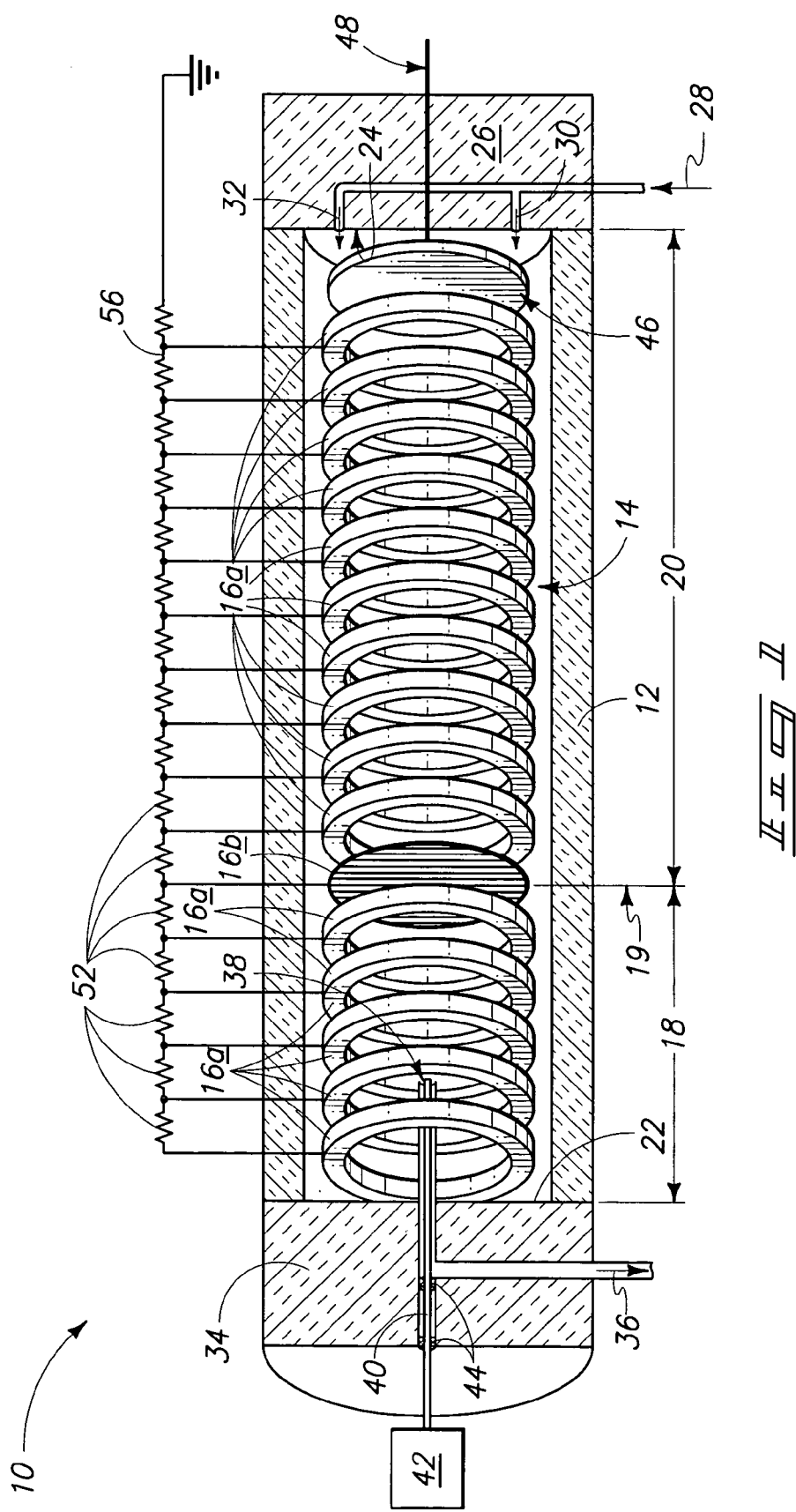
FIG. 1 is a perspective view of an ion mobility device in accordance with one aspect of the invention.

This disclosure of the invention is submitted in furtherance of the constitutional purposes of the U.S. Patent Laws "to promote the progress of science and useful arts" (Article 1, Section 8).

The invention encompasses ion mobility spectrometry (IMS) techniques where ions are mobilized to migrate through a drift fluid which is a liquid rather than a drift gas as conventionally utilized for IMS applications. Because ion diffusion constants are larger in liquids than in gases, the mobility of ions is significantly reduced when the drift gas is replaced with a drift liquid. Mobility through a given environment can typically be dependent upon, among other things, the size and shape of the ion.

Diffusion coefficients of a given ion in liquid such as water can typically be two or three orders of magnitude lower than the corresponding mobility in gases. Ions which can be separated using ion mobility techniques are not limited to any particular size and shape and can be an ionized form of a small molecule, either organic or inorganic, or can be an ionized form of a larger molecule including very large molecules such as, for example, peptides, proteins, nucleic acids and other bio-molecules. The liquid-phase IMS (LPIMS) techniques of the invention can be utilized for detection and/or separation of any of the types of molecules separated by gas-phase ion mobility spectrometry and, due to the reduced mobility constants in the liquid phase, the corresponding ion mobilities can be on the order of from about two thousand to about three thousand fold lower in the liquid-phase systems. Accordingly, the IMS systems of the invention can provide increased resolution for a given devices size relative to conventional gas-phase IMS systems.

One advantage of liquid-phase IMS relative to conventional gas phase techniques is that liquid-phase IMS can be conducted at or below ambient temperature. Although the liquid-phase IMS can be conducted at higher temperatures, desolvation of samples for liquid phase IMS can occur at or below ambient temperature. Gas-phase techniques on the other hand typically utilize elevated temperatures for desolvation purposes.

The ion mobility spectrometers and systems of the invention can be produced to be much smaller than conventional gas-phase IMS devices. In general, the devices of the invention can be scaled to approximately one tenth the size of a conventional IMS device with similar improved resolving power. Further, the differences in mobility constants of about three orders of magnitude allows instrumentation for liquid-phase ion mobility spectrometry to be as much as about three orders of magnitude smaller than standard gas-phase ion mobility instruments.

The scalability of liquid-phase IMS devices relative to conventional separation technologies, in conjunction with available advanced micro-machining methodology and techniques of the invention, can allow bio-analytical microsensors capable of ultra high resolution separations of complex bio-molecules to be produced. These devices can be placed upon a chip or an in vivo probe. Accordingly, the devices and methodologies of the invention can be adapted for a variety of biosensor and sensor-on-a-chip applications. While previously developed biosensors have been limited to single chemical or class of chemicals the LPIMS of the invention can potentially be multidimensional such that monitoring of multiple chemicals or classes of chemicals can be achieved. Liquid-phase IMS systems in accordance with the invention can include micro-scale or even nano-scale IMS devices with resolution power sufficient to detect and/or separate substances within most classes of molecules.

A liquid phase ion mobility spectrometer in accordance with one aspect of the invention is described generally with reference to FIG. 1. An ion mobility cell 10 can include a housing 12 having an internal chamber 14. Housing 12 can be formed, for example, utilizing a single tube such as that shown in FIG. 1. Alternatively, two or more interconnected or attached parts can be utilized to form a cylindrical or alternatively shaped housing (see FIG. 2). Housing 12 can be insulative and can be formed using any appropriate insulative material. Exemplary materials which can be utilized for housing 12 include but are not limited to ceramic materials, Teflon, and glass materials. Specific materials that can be utilized for housing 12 include low-temperature co-fired ceramic materials and polydimethylsiloxane. In the aspect of the invention depicted in FIG. 1, housing 12 can preferably be formed of one or more hollow ceramic cylinders.

Internal chamber 14 can be described as having two regions 18 and 20, with region 18 being referred to as an ionization region or ion trap region and region 20 being referred to as a drift or ion separation region. Chamber 14 has a longitudinal axis extending from a first end 22 of the chamber to a second end 24 of the chamber. The length and diameter of chamber 14 is not limited to any particular value. In particular instance (for example in some preparative applications), the length of the chamber can be similar to that of conventional gas-phase IMS chambers. In other applications, chamber 14 will be reduced on the order of from about 10 fold to over 1000 fold relative to conventional IMS devices. For many analytical applications, chamber 14 can have a length of less than or equal to about 2 mm. For particular micro-analytical devices, chamber 14 can have a maximum diameter of about 250 μm, with diameters of less than 250 μm being preferred.

Although regions 18 and 20 are depicted as having equivalent diameters relative to each other, it is to be understood that the invention contemplates alternative configurations where the diameter of region 18 differs from the diameter of region 20.

First region 18 is disposed proximate first end 22, and second region 20 is disposed proximate second end 24, with the longitudinal axis preferably passing substantially centralized relative to each of regions 18 and 20. An interface 19 disposed between ionization region 18 and drift region 20 can be described as being a partition between the two regions. Such partition or interface can be defined by an ion gate or electric potential well (described below) which blocks the passage of ions from region 18 to region 20 until the occurrence of a triggering event. It is to be understood that in particular aspects of the invention, no ion gate or other block to ion migration is utilized and therefore partition 19 is optional.

The ends of housing 12 can be covered and/or sealed utilizing, for example, end caps 26, 34. End caps 26 and 34 are not limited to any particular material and can preferably comprise an insulative material such as, for example, any of the materials discussed above with respect to housing 12. Materials used for the end caps can be the same relative to each other and/or housing 12, or the material utilized for one or more of caps 26 and 34 can differ relative to the housing and/or each other.

A plurality of electrodes 16a, 16b can be provided with in chamber 14. In the aspect of the invention depicted in FIG. 1, the plurality of electrodes can preferably comprise a series of evenly spaced electrodes which can include annular or "ring" electrodes 16a, and optionally one or more ion gate electrode 16b. Electrodes 16a and 16b are preferably parallel and concentric relative to each other and aligned substantially normal relative to the central axis of chamber 14. As will be understood-by one skilled in the art, the number of annular electrodes depicted is exemplary and can be any appropriate number to provide a desired electric field within the chamber.

As depicted in FIG. 1, the series of annular rings can be arranged axially along the length of chamber 14 with a first electrode proximate first end 22 and a last electrode proximate an ion collector 46 disposed at or near second end 24 of chamber 14, with gate electrode included in the series of electrodes.

In embodiments of the invention where an ion-migration block is utilized to partition the chamber, gate electrode 16b can be utilized as the ion-block. Gate 16b can comprise, for example, a conductive grid, a Bradbury-Nielsen-Shutter type ion gate, a Tyndall gate, or any alternative ion gate type electrode. Alternatively, an ion-migration block can be constructed at an interface between an ionization region 18 and drift region 20 by replacing gate electrode 16b with an annular ring type electrode, and shorting the electrode (at position 16b) to a neighboring or nearby electrode. Such shorting can occur, for example, by displacing or misaligning the electrode at position 16b to contact one or more other electrodes in the series thereby creating a short which can be reversed by realignment of the displaced electrode.

Any appropriately conductive material can be utilized for annular electrodes 16, or alternate electrode types used within chamber 14. Exemplary conductive materials which can be utilized include but are not limited to stainless steel, and gold.

Although FIG. 1 depicts gate electrode 16b, and the resulting partition 19, to be at a particular location within chamber 14, it is to be understood that the partition can be disposed at any location within the chamber. Preferably, partition 19 is disposed at an appropriate distance from end 24 to allow separation of ions within a particular sample to occur.

In the annular ring system depicted, a voltage difference can be provided within chamber 14 by applying a high voltage at the first ring electrode proximate first end 22 and grounding the last electrode at the opposing end thereby producing a voltage differential between the two opposing electrodes. Preferably, a decreasing voltage is applied to each of the electrodes along the series of electrodes such that a potential gradient is created along the axis of chamber 14. As shown in FIG. 1, a voltage divider 50 can be provided such that resistors 52 are disposed between each neighboring electrode 16a, 16b. Resistors 52 can be provided to have equal resistance such that a homogenous electric field is produced within chamber 14. Capacitors (not shown) can be utilized in combination with resistors to reduce current and/or voltage fluctuations along the ion drift length. Alternatively, the resistance of resistors 52 can vary or one or more of resistors 52 can be eliminated to produce a non-homogenous field for particular applications. In some applications, a single applied voltage within the chamber in association with a single continuous resistor can be preferred.

Although in many applications of the invention a constant homogenous field will be desired, the invention also contemplates providing a non-homogenous and/or time dependent field within chamber 14. Alternative or varied fields or field effects can be produced by for example, providing a quadrupole ion guide, an ion trap, an asymmetric wave form, Rf voltage, or other non-linear field(s) and/or applied voltage(s) in which ions migration occurs. These alternative fields can be useful for selecting ions based upon mass, charge, size and/or other characteristics.

In addition to differing numbers of annular rings, the invention contemplates utilization of alternative types of electrodes in place of ring electrodes 16a. Alternative electrodes which can be utilized for purposes of the invention include but are not limited to mesh type electrodes, planar electrodes and alternatively shaped electrodes (e.g. rectangular). Additionally, plated electrodes can be utilized where the electrode material (e.g. gold) is plated onto the inner surface of housing 12 at appropriate locations/intervals. Further, rather than utilizing a series of electrodes, a cylindrical tube constructed of a resistive conductive material such as resistive glass can be utilized. A voltage can be applied to one end of the resistive tube and will decrease as a function of distance such that a voltage potential gradient is created within the tube. This "resistive tube" construction allows an absence of separate resistors. Moreover, in an alternative embodiment, a field can be created along only a portion of the axis extending through regions 18 and 20.

Although FIG. 1 depicts resistors 52 as being disposed externally to housing 12, it is to be understood that the invention contemplates configurations where resistors (FIG. 2) are positioned within the internal space of chamber 14 or within the walls of housing 12.

Ion collector 46 can be, for example, a plate collector electrode such as a Faraday plate as shown in FIG. 1. Alternatively the ion collector can be a final electrode in the series of electrodes within the chamber, or any other appropriate ion collector. Ions can alternatively or additionally be detected utilizing one or more detection methods such as UV detection, fluorescence, laser induced fluorescence, electrochemical and mass spectroscopy.

Chamber 14 is at least partially and preferably entirely, filled with a drift liquid. Although the IMS devices of the invention are generally described as being liquid-phase separation devices, it is to be understood that the invention contemplates utilization of a supercritical fluid and/or pressurized gases as drift fluids within chamber 14. Accordingly, use of the term 'liquid' with respect to the drift fluid in the present description can be inclusive of supercritical fluids and pressurized gases.

In most applications, the drift liquid provided within chamber 14 will not be an electrolyte solution and can preferably be substantially free of ions (prior to introduction of sample ions to be anayzed). However, the invention contemplates utilization of an applied current for some applications, and the drift fluid in these instances can therefore comprise an electrolyte solution.

The drift liquid within chamber 14 is not limited to any particular solvent and can preferably be a non-polar or slightly to moderately polar solvent. A polar solvent can optionally be utilized where a background ion current is low. Additionally, the drift fluid can comprise two or more solvents from the same class or selected from differing classes of solvents. Exemplary classes of solvents which can be utilized in the fluid phase IMS drift chamber include saturated hydrocarbons, aromatic hydrocarbons, cyclic hydrocarbons, unsaturated hydrocarbons and paraffin. In particular applications, the drift fluid can preferably be an alcohol, such as decanol or methanol; or an oil, such as mineral oil. A combination of solvents can be utilized to obtain a desired polarity to enhance or maximize ion separation in some instances. Further, a chiral solvent can be utilized to assist in separation of ionized chiral molecules. As indicated above, a current can be useful for some separation applications and an appropriate electrolyte solution can be utilized as the drift liquid.

A voltage differential across the length of IMS chamber 14 is not limited to any particular value. In many applications, the voltage will be relatively high as compared to typical voltages utilized in a conventional gas-phase IMS system having similar or identical drift tube dimensions. Due to the absence of electrolytes within the drift fluid in most instances, the voltage provided across the drift chamber can be used to create an electrostatic field and thereby separate sample ions without a current generated by electrolytes. Accordingly, heat generation can be minimized which can in turn avoid or minimize loss of resolving power. Additionally, the absence of applied current can reduce or minimize noise thereby allowing for direct ion detection in some applications.

The voltage difference across drift chamber 14 can depend upon the column size, the sample or ions being analyzed, the drift liquid and other system parameters as will be recognized by those knowledgeable in the field. Although a voltage difference higher than 100 kV can be utilized, a preferred voltage differential can be from about 10 kV to about 100 kV. Accordingly, an appropriate voltage of up to ±100 kV can typically be applied. In particular applications an applied voltage of from ±3 kV to about ±10 kV will be sufficient for ion detection and/or separation. (For purposes of the present description, a general indication of applied voltage can be a positive or a negative voltage unless specifically indicated otherwise).

Assembly 12 can additionally be provided with a fluid source 28 having one or more inlets 30, 32 into the chamber. Fluid source 28 is configured to provide liquid within chamber 14 which can be referred to as a drift liquid or 'mobility liquid'. Source 28 can alternatively be a supercritical fluid or gas source. A chamber outlet 38 can be provided at first end 22 opposing inlets 30, 32. Outlet 38 can be connected to fluid passageway 36 which can be a drain or which can be connected to a pump (not shown). Alternatively, a pump can be associated with fluid source 20 to supply fluid into the chamber. In particular applications, a flow of drift fluid is provided through chamber 14 flowing from inlets 30, 32 toward first end 22 and exiting through passageway 36, thus flowing counter to the direction of ion migration through the electric field. The counter-flow of drift liquid can, in some instances, can achieve greater separation than would occur in the absence of such counter-flow.

Although inlet passageways 30 and 32 and outlet passageway 36 are shown as passing through end caps 26 and 34, it is to be understood that the invention contemplates alternative placement of such inlets and outlets, for example, through housing 12.

A portion of passageway 36 can also function as an inlet port as depicted in FIG. 1. A transfer tube 40 can be utilized to supply or transfer a sample to be analyzed from a sample supply 42 into chamber 14. Transfer tube 40 can be, for example, a needle or a capillary and sample supply 42 can be, for example a syringe, an injection coil, and/or an appropriate holding vessel. Additionally, in particular applications source 42 can comprise a pump for injecting a sample into and/or through transfer tube 40. Transfer tube 40 can comprise an insulative material or a non-insulative material. Exemplary materials for transfer tube 40 include, but are not limited to fused silica and stainless steel.

O-rings or other seals 44 can be provided surrounding tube 40. Although the figure depicts transfer tube 40 as being disposed within a common passage used for the drift fluid outlet, it is to be understood that the invention contemplates providing separate ports for fluid outlet from, and sample introduction into, chamber 14.

Sample supply 42 can comprise a sample containing molecules to be analyzed which can be ionized either during delivery into chamber 14 or upon introduction into ionization region 18. Samples introduced into chamber 14 for analysis can preferably comprise liquid samples containing molecules of interest in a solvent. Typically, the solvent can be polar and in particular instances, the sample solvent will be water.

For aqueous and other polar solvent-comprising samples, a preferred method of ionization of molecules within the sample can comprise an electro-dispersion ionization technique. In this technique, a voltage is applied to transfer tube 40. An aqueous or other sample containing solvated components of interest can be introduced through the charged transfer tube into region 18 of chamber 14. For purposes of describing the electro-dispersion ionization technique, region 18 can be referred to as a de-solvation region of the chamber.

Voltage applied to transfer tube 40 can be up to about ±100 kV volts, with applied voltages of from greater (or less) than 0 kV to about ±10 kV being typically sufficient for electro-dispersion ionization to occur. Depending upon the voltage on the sample solution, the sample can break apart or electro-disperse in the presence of the electric field within chamber. 14. Such electro-dispersion can form tiny microdroplets of sample that carry an electrical charge. Water or other sample solvent becomes dispersed and/or dissolves into the drift solvent within chamber 14. The drift solvent can preferably be one which differs from the sample solvent, is non-aqueous and/or is a solvent in which the sample solvent is only partially soluble. Preferably, the sample solvent is at least slightly soluble in the drift solvent. Eventually, the charge on the sample micro-droplets results in an ultimate release or ejection of ions from droplet surfaces.

The above description of the electro-dispersion process is theoretical based upon observations of the ionization process in accordance with the invention. However, the invention is in no way intended to be limited by such theory. Regardless of the exact events that occur during the electro-dispersion, released or ejected ions are at least partially de-solvated relative to the sample solvent although, in particular instances it is possible that the ejected ions may be coordinated with one or more water (or alternative sample solvent) molecules. Mobility studies of ions produced by the electro-dispersion ionization technique indicate mobility behavior consistent with molecular ions or ions having very few coordinated water molecules.

Exemplary alternative IMS device configurations which can be utilized with electro-dispersion ionization techniques are discussed with reference to FIGS. 2–3. As shown in FIG. 2, an alternative IMS device 110 can be provided with a sample inlet port 154 which is independent of a transfer tube such as transfer tube 40 described above. Inlet port 154 can be described as being comprised by a sample passageway into an ion migration chamber 114. A sample can be introduced into chamber 114 by passing through inlet 154 and passing through or over an ionization plate 156 disposed at a first end 122 of chamber 114. A voltage can be applied to the ionization plate such that sample passing through or over the plate become charged and, upon entry into the electric field within chamber 114, electro-dispersion ionization can occur. The voltage applied to plate 156 can be as described above with respect to injection tube 40.

Referring to FIG. 3, such shows an alternative inlet port configuration where a conductive component 158 is provided within passage 154. A voltage is applied to component 158 such that a sample containing molecules of interest which is passed through passage 154 becomes electro-dispersed upon entering the effects of the electric field within chamber 114. Conductive component 158 can be, for example, a ring, wire, plate, cylinder or any other appropriate configuration to which an appropriate voltage (described above) can be applied.

The various described electro-dispersion ionization techniques can allow the drift chamber IMS separation to occur in the absence of any ionization gate or trap region. This non-gated IMS aspect of the invention can be achieved by pulsing sample through the charged sample inlet passage, and/or by pulsing voltage on the inlet tube, voltage plate, ring, wire or other conductive component being utilized in association with the sample inlet passage. Accordingly, the invention encompasses non-gated liquid-phase IMS systems. However, any of the electro-dispersion ionization configurations can additionally be used in conjunction with an ion gate or other ion-migration block or trap. Hadamard, Fourier, or alternative time dispersed transformation methods may be utilized to enhance ion throughput. Although a physical ion gate can be utilized in conjunction with time dispersed transformation, typically, the time dispersion methods will be performed in an absence of an ion gate.

It is to be understood that the alternative electro-dispersion ionization source configurations illustrated in FIGS. 1–3 are exemplary and are not intended to limit the scope of the invention. In general, the invention contemplates utilization of any variation on the described features which can allow a charge to be imparted to a liquid sample during delivery into, or at the time of entry into an electric field present in a solvent which differs from the sample solvent. Further, the electro-dispersion ionization techniques are not limited to IMS applications and can be adapted to other liquid-phase analytical techniques as well.

Alternative ionization techniques can be utilized in place of the electro-dispersion ionization described above. Accordingly, one or more alternative ionization sources (not shown) can be provided in association with ionization region 18. Exemplary ionization techniques which can be utilized for generating ions for analysis in accordance with the invention include, but are not limited to, laser ionization, photo ionization, electrochemical ionization and radioactive ionization sources.

Regardless of the method of ionization utilized, once ions are introduced into chamber 14, partition 19 can be utilized to "trap" ions or otherwise block ions from migrating from region 18 into drift region 20 until a triggering event which unblocks the partition. Where an ion gate (gate electrode) 16b is utilized, the triggering event can typically be a voltage applied on the electrode which can result in a pulse or packet of ions passing through the gate across partition 19. A appropriate voltage pulse for triggering the passage of ions can depend upon the particular gate and various other factors including drift solvent, chamber size, and particular ions to be analyzed. A typical pulse width can be from about 0.2 seconds to about 5 seconds, with shorter pulses being preferred. The pulse frequency should preferably be slower than the arrival frequency of the largest ion of interest. Accordingly, the pulse frequency will typically be from about 0.1 Hz to about 0.4 Hz (every 25–100 seconds).

As ions migrate through the drift fluid toward collector electrode 46, the ions can be effectively separated based upon their mobility through the drift liquid. Collection of ions at the collector electrode can be detected as a current signal 48. Accordingly, the time of migration through drift portion 20 of chamber 14 can be utilized to detect, characterize and/or identify molecules present in the sample.

A second aspect of the invention is described with reference to FIG. 4. An ion mobility spectrometer assembly 10 is shown having alternative housing and other features relative to the embodiment depicted in FIG. 1. The primary difference between cell 10 shown in FIG. 4 and that described above is that rather than being cylindrical, housing 12 is a block of material comprising two halves into which a hollowed out chamber 14 has been fabricated. Block housing 12 can be formed utilizing a variety of materials including, but not limited to, Teflon, or any of the alternative housing materials discussed above. Block 12 can be fabricated to provide grooves for insertion and support of a plurality of annular ring electrodes (ring guards) such as those depicted in FIG. 1. Alternative electrode types described above can similarly be used within the device configuration of FIG. 4. Additionally, any of the ionization sources and ion gate or other ion-migration blocking (or absence thereof) configurations described above can be utilized in conjunction with the chamber configuration shown in FIG. 4.

Figure 4:
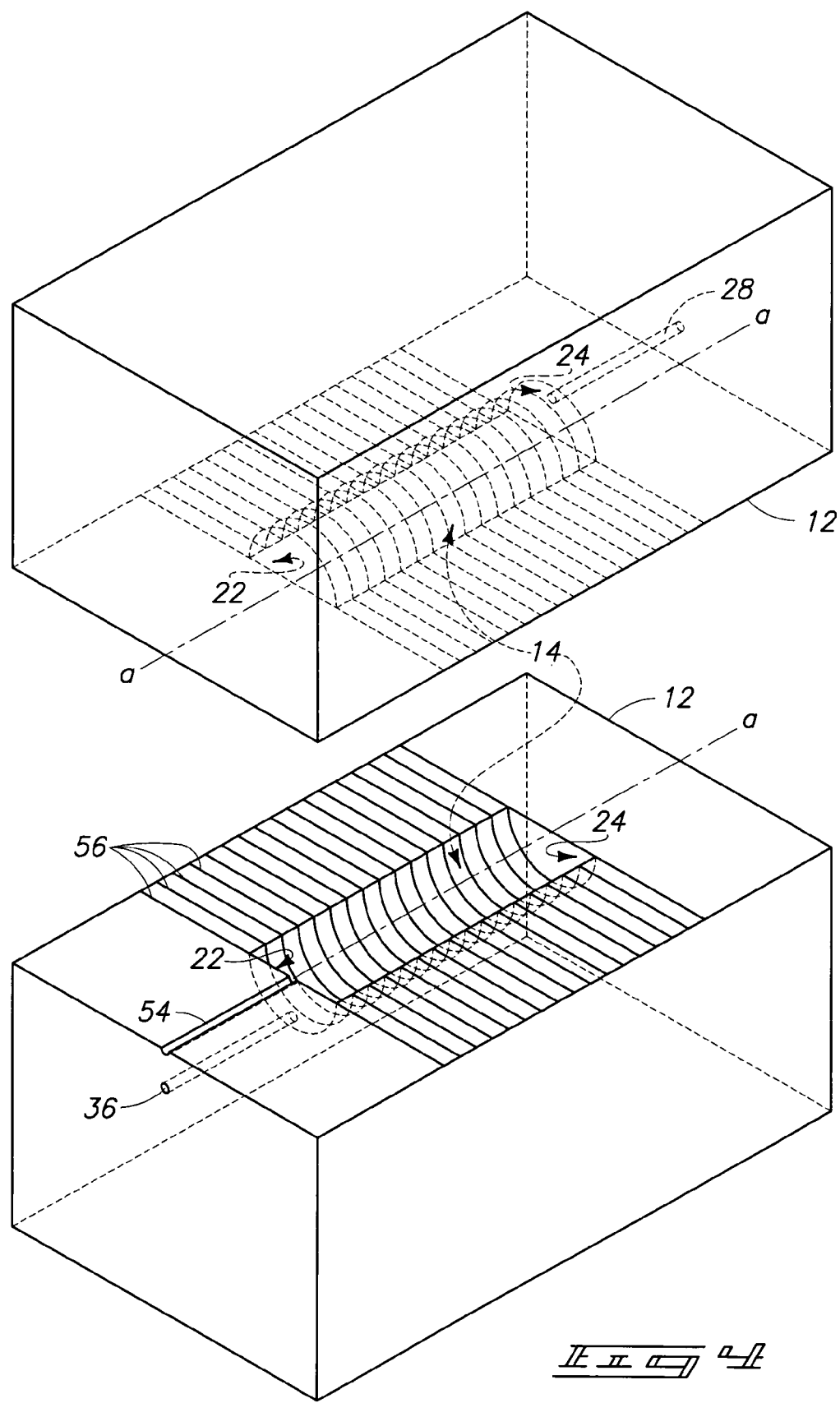
FIG. 4 is a perspective view of an alternatively configured device relative to the aspect shown in FIG. 1.

As shown in FIG. 4, an inlet 28 can be provided through block housing 12 to provide fluid access for supplying drift liquid into chamber 14. Similarly, a drain or fluid outlet 36 can be provided at the opposing end for removal of the drift liquid from the ion mobility chamber. A sample injection portal 54 can be provided to allow insertion of a sample transfer capillary or needle or other sample transfer tube 40, or can be equipped with any of the electro-dispersion ionization components described above.

Any of the various detection techniques described above can be utilized in conjunction with the IMS cell depicted in FIG. 4. Block housing 12 can be configured such that wiring 56 occurs at the interface between the two portions of housing block 12. Resistors can be provided serially between annular ring electrodes by providing external resistors, resistors within housing portion 12 or resistors internal to chamber opening 14.

As discussed above with respect to FIG. 1, ions can be introduced into the device shown in FIG. 4 at first end 22 and can be mobilized to migrate toward second end 24 by providing a homogenous or non-homogenous electric field. An ion collector such as a grounded annular ring electrode or Faraday plate can be provide at second end 24 and can transfer current information via an appropriate signal pathway provided through housing 12.

Figure 5:
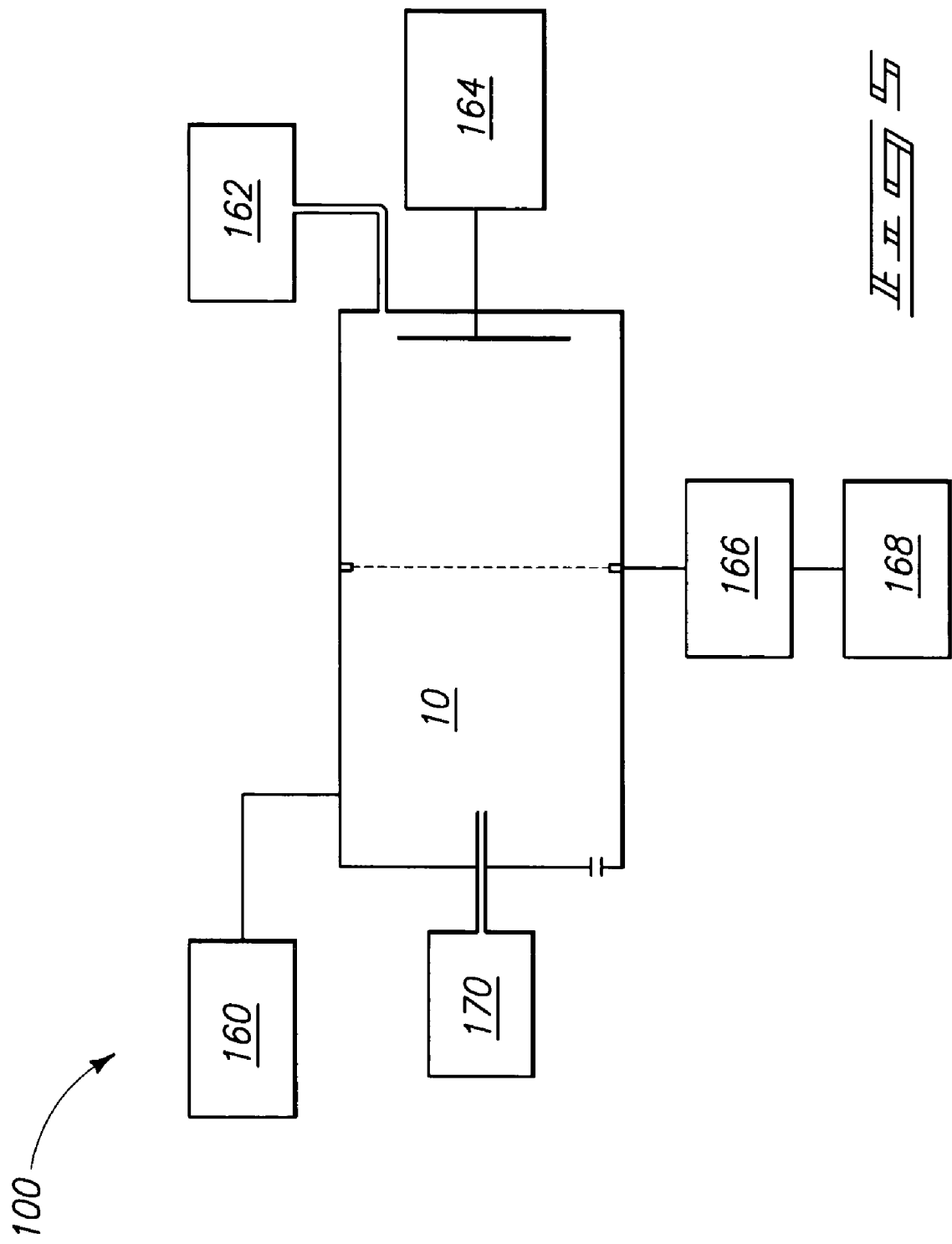
FIG. 5 is a schematic diagram of an ion mobility spectrometry system in accordance with an aspect of the invention.

Referring to FIG. 5, such shows an exemplary configuration of an IMS system in accordance with the invention. An IMS separation cell 10 can be provided having any of the features or combinations thereof described above. A sample injector 170 (which can replace or include sample source 42) can be configured to provide a sample into a first end of device 10. In particular aspects, injector 170 can include a pump. In particular instance, injector 170 can be automated to inject or provide a sample at a predetermined time, rate, etc. Alternatively, where manual sample delivery is desired, injector 170 can be omitted.

Where device 10 comprises a gate electrode, a gate driver (such as a pulse generator) can be provided to provide an appropriate electrically pulse(see above) to trigger a passage of ions toward the collector 46 disposed at the opposite end of the mobility cell. A gate driver controller 168 can be provided for proper control and/or timing of pulse delivery from gate driver 166. Where device 10 comprises a reversible-short type ion trap system, gate driver 166 can be a mechanical and/or electrical device for temporary removal of the short either by a repositioning of a displaced electrode, or otherwise removing a shorting contact. Accordingly, controller 168 can be configured to time or otherwise control the triggering event driven by driver 166.

Ions collected at collector 46 can generate a signal which can be transferred from collector 46 to a detector 164. Detector 164 can comprise, for example, an amplifier and/or a data processor for collecting and/or processing data. Detector device 164 can further comprise a computational device which can be either integrated with or connected to the processor and/or amplifier portions of the detection device. The controller portion of detector 164 can either be the same or can be independent of controller 168.

System 100 can additionally comprise one or more voltage supplies 160. In some instances, it can be desirable to provide independent voltage supplies for one or more of the electrode generating the electric field, the ion gate and the ionization source.

A pump 162 can be provided for pumping liquid (or supercritical fluid or pressurized gas) into an inlet of device 10. Alternatively, pump 162 can be associated without the outlet portion of device 10 and can pump liquid out of the mobility chamber. In particular instances, pump 162 can be a pump system utilized for recycling fluid through the ion mobility separation cell. Drift fluid can preferably be provided directionally through device 10 from the end proximate detector 46 toward the sample inlet such that a counterflow of drift fluid is provided relative to the direction of ion migration within the chamber.

In general, a method of analyzing a sample by ion mobility spectroscopy performed in accordance with the invention can comprise providing a liquid sample containing a solvent and one or more various molecular components of interest. The sample can be subjected to ionization techniques such as those described above either during or after injection of the liquid sample into the IMS device. In general, with reference to FIG. 1, an ion mobility analysis device 10 is provided which has a chamber 14 disposed within housing 12. The chamber contains a drift liquid and a sample is introduced into the drift liquid at a first end 22 of the chamber. Ions can be generated within the sample utilizing any of the ionization techniques discussed above.

In particular instances, the sample can comprise molecules to be analyzed in a first solvent, usually water. A voltage is applied to transfer tube 40 and the sample is passed through the charged transfer tube. The introducing of the sample through the charged tube can impart a charge onto the sample resulting in charged sample droplets. As the sample enters the drift liquid and the electric field, the droplets are electro-dispersed, thereby releasing or ejecting ions into the ionization portion of the internal chamber 14. The resulting ions are at least partially de-solvated with respect to the first solvent as they enter the second solvent.

Ions introduced into or generated within ionization region 18 are trapped or otherwise blocked from migrating into drift region 20. Blockage of migration of the ions is removed by a triggering event at the interface between ionization region 18 and drift region 20. Such triggering event can be a voltage pulse applied to an ion gate, or can be removal of a short between electrodes as described above. Upon the occurrence of a triggering event, a pulse or packet of ions is released across partition 19 to enter drift region 20. The release ions are subjected to an electric field which can preferably be a homogenous electric field throughout at least the separation region of chamber 14. Differing ionized components are separated relative to one another based upon their relative ion mobilities through the particular drift fluid utilized in the chamber. In most instances, the drift fluid will lack electrolytes and the field will accordingly be an electrostatic field.

In an alternative method of the invention, ions are generated by pulsing a sample through a charged ionization zone or by pulsing a voltage across an ionization component. The pulsed/pulse-charged sample is electro-dispersion ionized by the effects of the electric field within the liquid filled IMS chamber upon the charged sample. The mobilized ions are allowed to migrate in the absence of any ion-migration block.

Once mobilized, ions are collected at an ion collector 46 and such collection results in a generation of a signal which can be passed from collector 46 via signal passage 48 to an appropriate detector and signal processing equipment. During one or more of sample injection, sample ion trapping and ion mobilization and separation events, a flow of drift fluid can be provided through the chamber from the detector end toward the sample inlet end to provide a counter flow of drift fluid relative to the direction of ion migration.

An elapsed time between the triggering event which releases ions at interface 19, (or pulse ion generation in the absence of a gate), and the detection of such ions at collector 46 can be utilized to detect, separate and/or identify the components within the sample. Such separation can be utilized for singly charged or multiply charged ions. Accordingly, the methodology of the invention can be utilized for both analytical and preparative separations of bio-molecules, industrial molecules, pharmaceuticals and other molecules including both organic and inorganic molecules. In preparative applications, component ions can be eluted and due to their separation relative to one another, can be collected in isolated or purified form.

EXAMPLE 1

Liquid Phase Ion Mobility for HCl in Decanol

Figure 6:
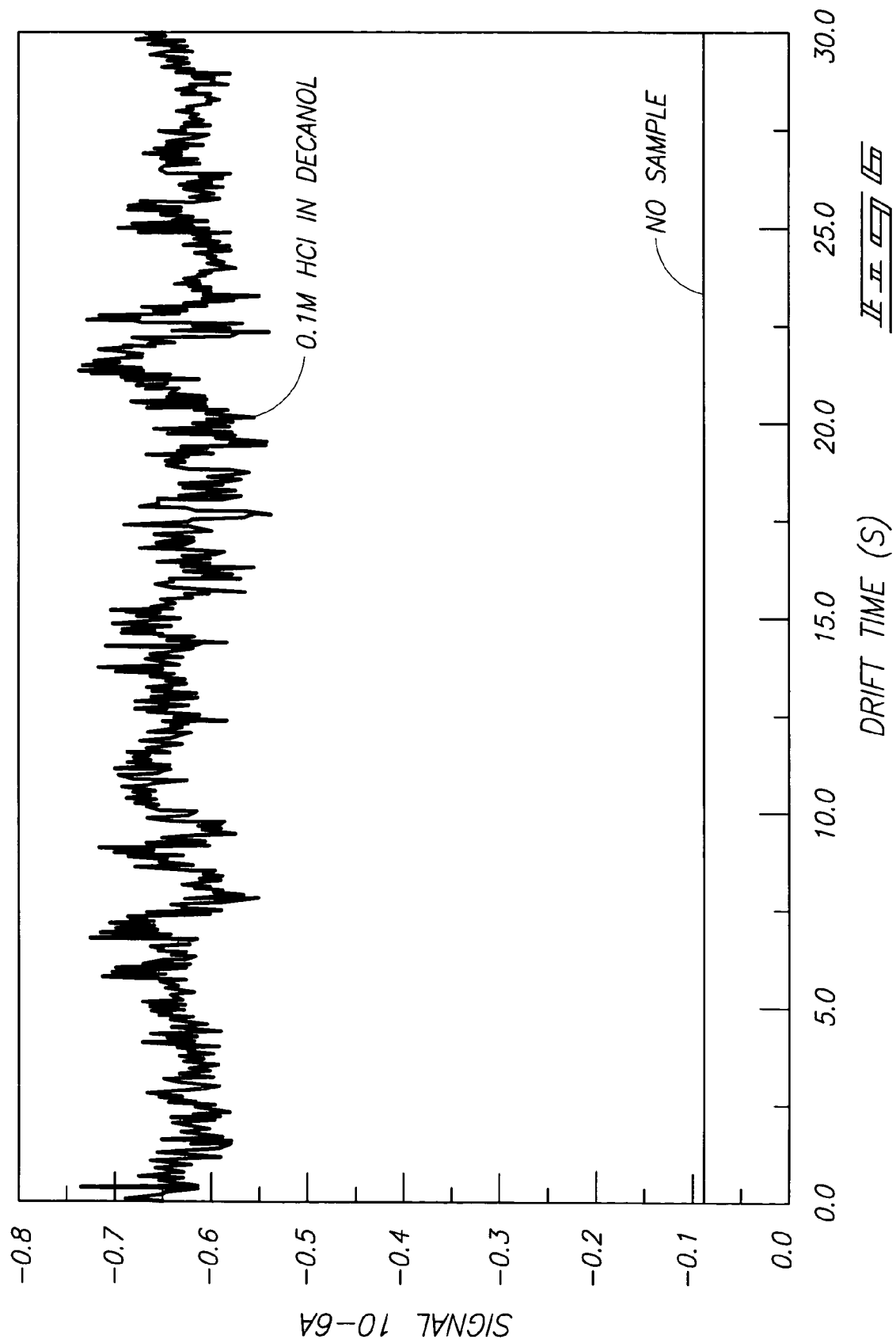
FIG. 6 shows the ion signal obtained for HCl through decanol in the absence of an ion gate.

An aqueous solution of 0.1 M HCl was injected at one µL/min for 30 seconds into the liquid phase of a liquid phase IMS device. The device utilized for the HCl migration analysis was a Teflon block device similar to that shown in FIG. 4 having a 20 mm overall chamber length. For the present study, no ion gate or other potential well was applied thereby allowing ions in the injected sample to pass directly through the device without being trapped at an interface. The drift fluid utilized was decanol. As show in FIG. 6, the resulting current obtained at the collection electrode was around 650 nAmps.

EXAMPLE 2

Liquid Phase IMS Analysis of $NH_4^+$

Figure 7:
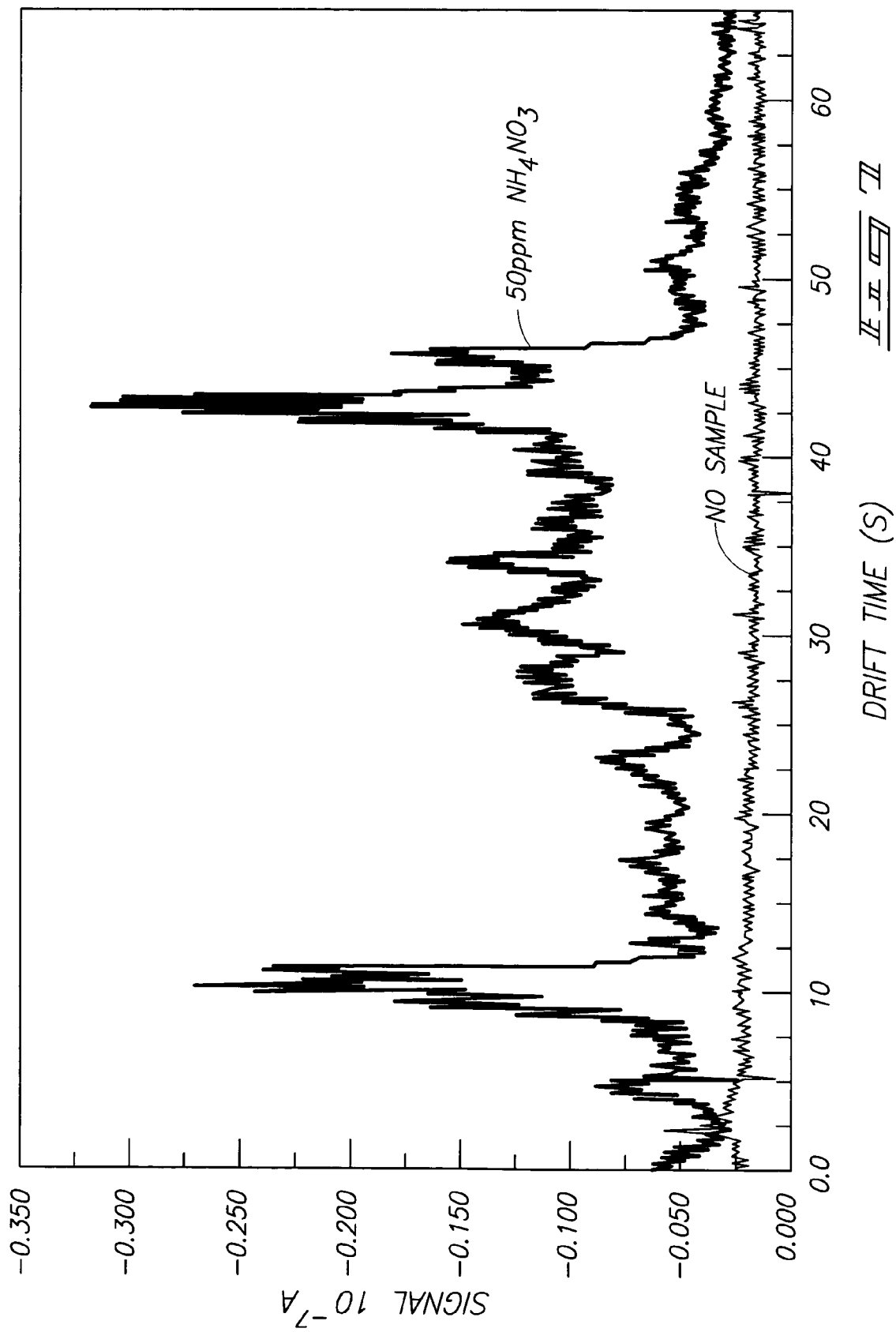
FIG. 7 shows a liquid-phase ion mobility spectrum obtained for $NH_4^+$.
Figure 7:
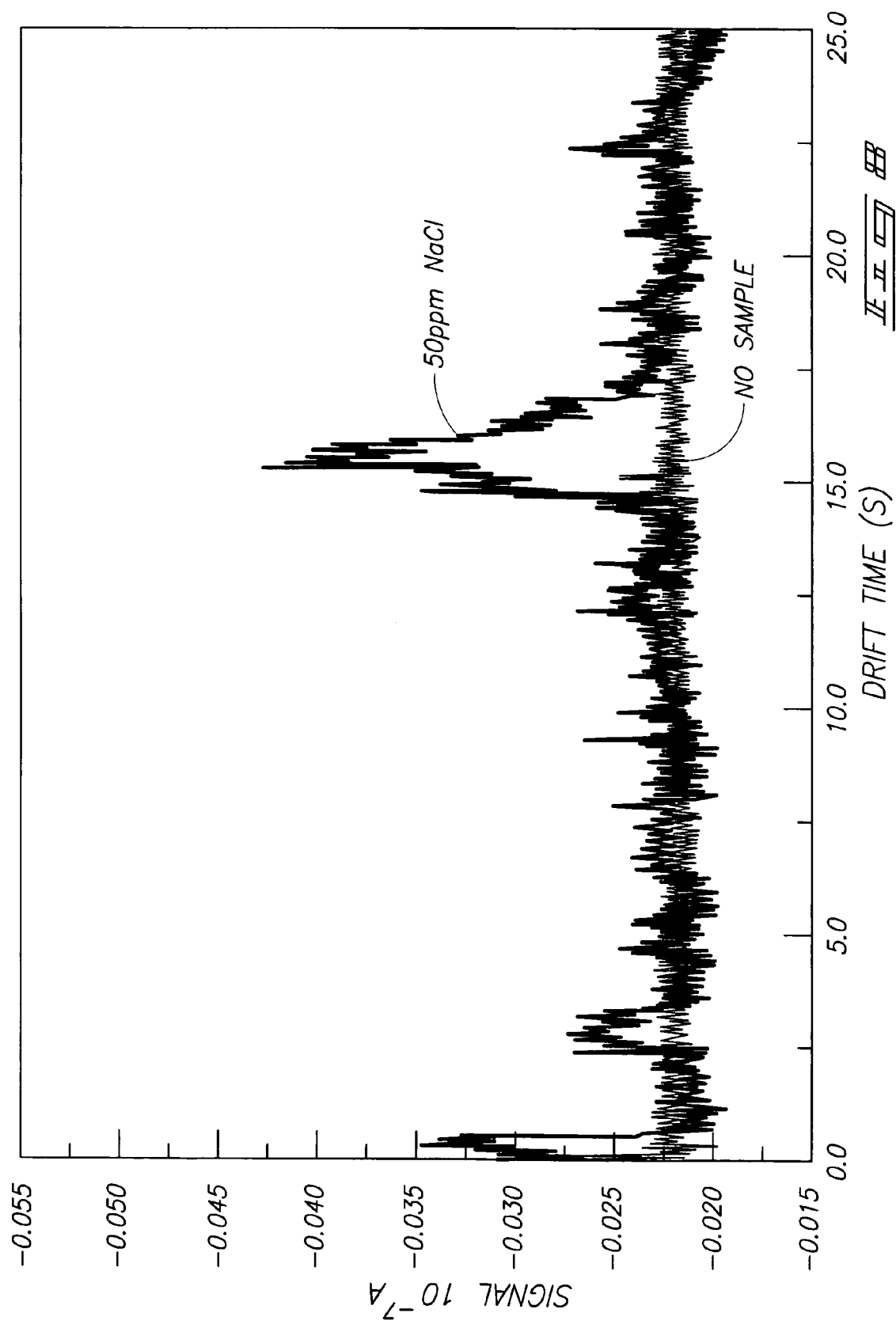

A liquid phase ion mobility spectrum was obtained by injecting 0.25 µL/min of an aqueous solution containing 50 ppm $NH_4NO_3$ into a mineral oil liquid phase. A 12.25 mm drift tube length was utilized with a Teflon tube housing. An ion gate was pulsed open for 5 seconds. A 3 kV potential was placed on the first ring electrode, the last ring electrode was grounded and each of 16 electrodes within the chamber was connected in series with intervening 1 MΩ resistors. Ionization of the sample was achieved utilizing electro-dispersion ionization. The resulting spectrum is shown in FIG. 7. The complex spectrum may be indicative of partially solvated (with coordinated water) of the $NH_4^+$ ions. Improved desolvation can be achieved utilizing a more polar drift liquid.

EXAMPLE 3

Liquid Phase IMS Analysis of $Na^+$

An aqueous sample containing 50 ppm of NaCl was introduced into a mineral oil liquid phase at a rate of 1 µL/min. A 1 kV voltage was applied to the sample injection needle and the ion gate was pulsed for 0.2 seconds. The resulting spectrum shown in FIG. 8 indicates a resolving power of about 15. The resolving power can be increased by applying increased voltage on the sample transfer tube and/or varying the gate pulse width. The gate utilized for obtaining the sodium ion liquid phase IMS spectra was a reversible potential well type (described above).

EXAMPLE 4

Liquid Phase IMS Analysis of NaCl Utilizing an Alternative ion Gate

Figure 9A:
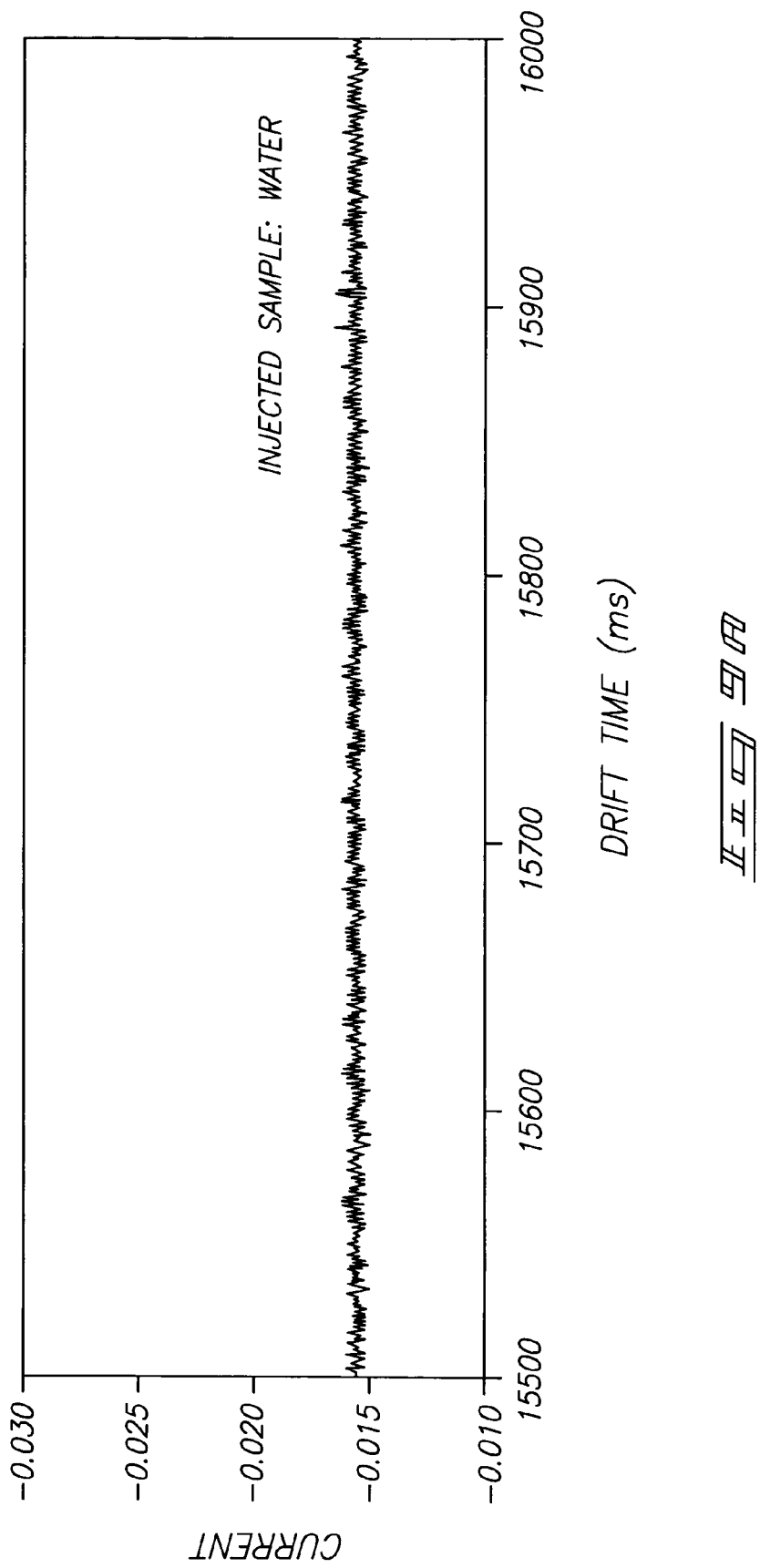
FIG. 9 shows a liquid phase ion mobility spectrum for water (9A) and $Na^+$ (9B) utilizing a Bradbury-Nielsen-Shutter type ion gate.
Figure 9B:
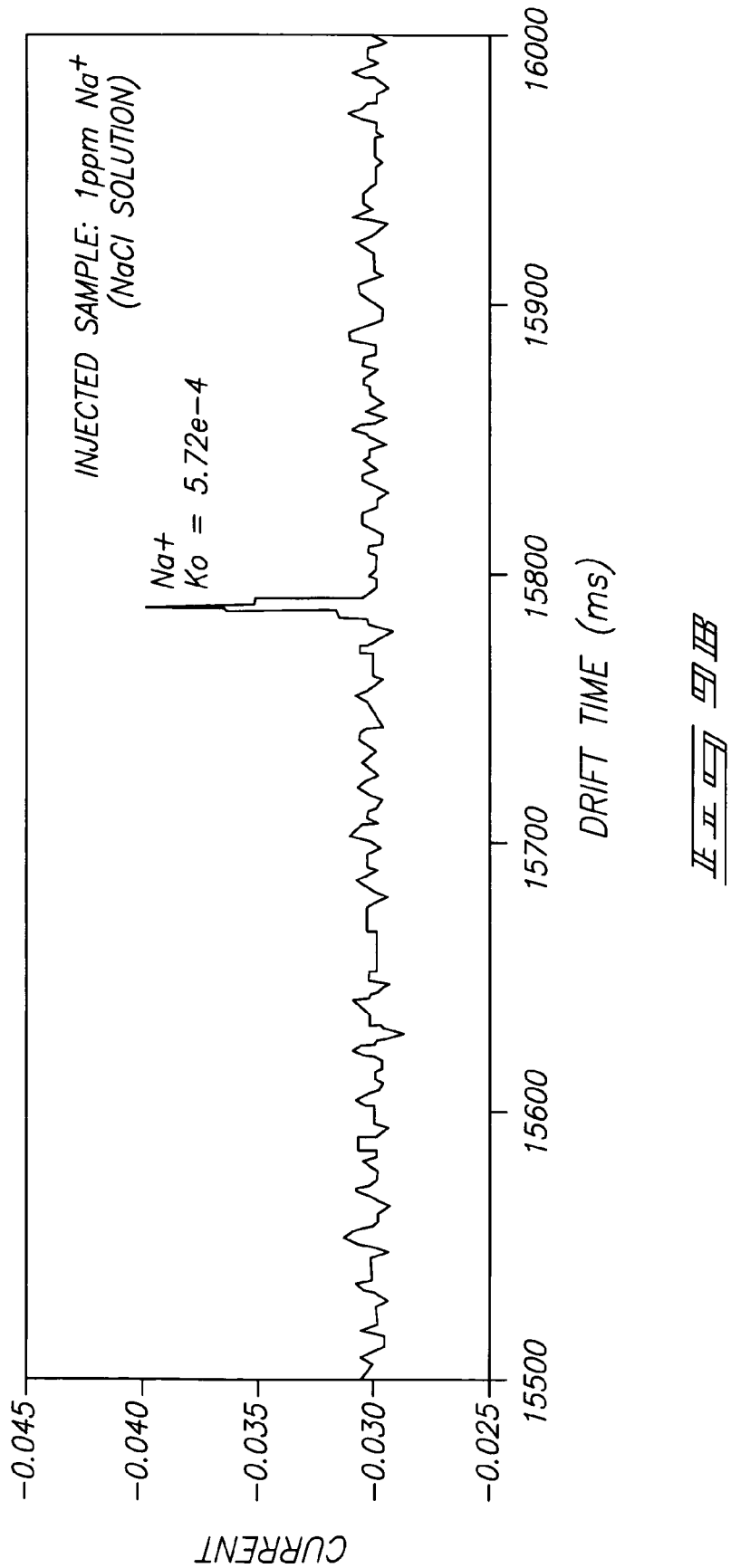

A 2 µL sample of 1 ppm aqueous solution of NaCl was injected into a mineral oil liquid phase within a 3.8 cm length drift tube. The voltage on the first electrode was 2 kV. A Bradbury-Nielsen-Shutter type ion gate was utilized and was held open for 100 ms. Mineral oil was provided at a counter flow rate of 1 ml/minute. The resulting spectrum is shown in FIG. 9B and is compared to a 2 µL sample of pure water (FIG. 9A) analyzed under otherwise identical conditions. The $Na^+$ analysis resulted in a single peak with a $K_0$ (ion mobility $cm^2V^{-1}s^{-1}$) value of $5.7 \times 10^4$ (similar to the calculated value of $5.3 \times 10^{-4}$ for $Na^+$ in water). The resulting spectrum indicates a resolving power of approximately 3000.

EXAMPLE 5

Electro-dispersion Ionization Study

A series of samples were used to analyze electro-dispersion ionization (EDI). The solutions studied included aqueous bromothymol blue, aqueous ammonium hydroxide, aqueous acetic acid, a 50:50 methanol: water mixture, aqueous arginine, aqueous lysine, and aqueous serine. These samples were compared to HPLC grade water and 18 MΩ water samples. The studies were conducted at room temperature. Samples were introduced at flow rates of from greater than 0 to 5 µl/min into a glass IMS housing filled with decanol drift liquid. Field strengths of from 0 to 100,000 V/cm was utilized within the drift chamber (no ion gate or other mobility block was used).

Samples were introduced using a capillary with an applied voltage of from 0 to ±10 kV. When no voltage was applied, no current was detected for any of the samples. With a voltage of from about 1 kV to about 2 kV currents were measured but no "spraying" dispersion was observed. When the voltage applied to the capillary was about 3 kV or higher, spray dispersion was observed in each case and currents were measured.

In samples that were analyzed with an applied voltage of 10 kV, current and spray electro-dispersion were observed to occur at coinciding intervals due to an ion ejection rate which exceeds the sample flow rate.

The data obtained from the studies indicated that increased current results when the charge on the capillary is increased. The current can also increase with increased sample flow rates. The distance between the capillary and the ion detector did not significantly affect measured current. For some samples (lysine (aq) and arginine (aq)), increased sample concentration produced a detectable current increase relative to samples having a lower concentration of the respective amino acid. The results of these ionization studies indicate that electro-dispersion ionization is an effective ionization technique that can be useful for ion mobility separations and other liquid-phase separation methods.

Although the IMS system of the invention has been described above in terms of a time-of flight type IMS system, it is to be understood that the concepts and applications of the invention can be adapted for utilization in alternative IMS systems including differential mobility spectrometry (DMS), field asymmetric ion mobility spectrometry (FAIMS), and differential mobility analysis (DMA) systems, as well as systems yet to be developed. Accordingly, the invention contemplates liquid-phase, supercritical fluid-phase and pressurized gas-phase ion separation and analysis utilizing DMS, DMA, and FAIMS type devices.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. An ion mobility spectrometer comprising:
   a housing;
   a chamber within the housing having a first end, a second opposing the first end, and a central axis extending from the first end to the second end, the chamber comprising a first region electrically partitioned from a second region by at least one of an ion gate and an electric potential well;
   a plurality of annular electrodes within the housing, the plurality of annular electrodes being configured to provide an electric field along at least a portion of the central axis of the chamber; and
   a drift liquid within the chamber.

2. The spectrometer of claim 1 further comprising an ionization source associated with the first region, the ionization source being selected from the group consisting of a photo-ionization source, a laser ionization source, a radiation ionization source, an electrochemical ionization source, and an electro-dispersion ionization source.

3. The spectrometer of claim 1 wherein the drift liquid is non-polar.

4. The spectrometer of claim 1 wherein the drift liquid is substantially electrolyte free.

5. The spectrometer of claim 1 wherein the first region is electrically partitioned from the second region by a Bradbury-Nielsen-Shutter ion gate.

6. The spectrometer of claim 1 wherein the first region is electrically partitioned from the second region by a Tyndall gale.

7. The spectrometer of claim 1 wherein the first region is electrically partitioned from the second region by an electric potential well created by a reversible short between two electrodes comprised by the plurality of annular electrodes.

8. The spectrometer of claim 1 further comprising an ion collector disposed within the second region proximate the second end of the chamber, the ion collector comprising at least one of an annular electrode and a Faraday plate.

9. The spectrometer of claim 1 wherein the electric field is electrostatic.

10. The spectrometer of claim 1 wherein the electric field is homogenous throughout the second region of the chamber.

11. An ion mobility analysis system comprising:
    a device housing;
    a chamber internal to the housing, the chamber comprising an ionization region, an ion separation region and a longitudinal axis passing centrally through the ionizing region and the ion separation region;
    a series of annular electrodes within the chamber, at least some of the electrode in the series being aligned substantially parallel relative to each other and substantially normal to the longitudinal axis;
    a sample inlet at a first end of the device;
    an ion collector within the chamber proximate a second end of the device;
    an ionization source associated with the ionization region;
    a liquid within the chamber, the device being configured to provide an electric field within the chamber such that ions present in the chamber migrate through the liquid toward the electrode collector; and
    a reversible ion-migration block defining an interface between the ionization region and the ion separation region, the ion-migration block being configured to block passage of ions from the ionization region to the ion separation region until an occurrence of a triggering event which reverses the block allowing ions to migrate from the ionization region into the ion separation region.

12. The ion mobility analysis system of claim 11 wherein the reversible ion-migration block comprises an ion gate electrode, and wherein the triggering event is a voltage pulse applied to the ion gate electrode.

13. The ion mobility analysis system of claim 11 wherein the reversible ion-migration block comprises a short between two annular electrodes comprised by the series of annular electrodes, and wherein the triggering event is a removal of the short.

14. The ion mobility analysis system of claim 11 further comprising:
    a fluid inlet associate with the second end of the device; and
    a fluid outlet associated with the first end of the device, wherein the liquid is flowed through the chamber from the second end to the first end during the ion mobility analysis.

15. The ion mobility analysis system of claim 11 wherein the sample inlet comprises a sample injection capillary.

16. The ion mobility analysis system of claim 15 wherein the sample injection capillary is charged.

17. A method of conducting ion mobility analysis, the method comprising:
    providing a chamber containing a fluid comprising at least one of a liquid and a supercritical fluid;
    introducing a sample into the chamber at a first end;
    mobilizing ions within the sample to migrate through the fluid; and
    detecting the mobilized ions at a second end of the drift chamber.

18. The method of claim 17 wherein the chamber is comprised by an ion mobility spectrometer comprising a housing and a plurality of ring electrodes disposed within the housing along a longitudinal axis of the chamber.

19. The method of claim 18 wherein the plurality of ring electrodes comprises a first ring electrode and a last ring electrode, and wherein the mobilizing comprises providing a voltage difference between the first ring electrode and the last ring electrode, the voltage difference producing an electrostatic field along the longitudinal axis.

20. The method of claim 18 wherein the mobilizing comprises removal of a short between two ring electrodes comprised by the plurality of ring electrodes.

21. The method of claim 18 wherein the spectrometer comprises a gate electrode disposed between the first end and the second end of the drift chamber and wherein the mobilizing comprises applying an electrical pulse to the gate electrode.

22. The method of claim 18 wherein the plurality of ring electrodes are associated with a voltage divider to produce a homogenous electric field throughout the drift chamber.

23. A method of analyzing a sample comprising:
    providing an ion mobility analysis device having a chamber disposed within a device housing, the chamber containing a drift liquid;
    introducing a sample into a first end of the chamber;
    generating ions within the sample; and
    mobilizing the ions to migrate through the drift liquid toward a second end of the chamber.

24. The method of claim 23 wherein the mobilizing comprises providing a homogenous electric field along a longitudinal axis of the chamber.

25. The method of claim 23 further comprising passing at least some of the ions through an ion gate disposed between the first end and the second end of the chamber.

26. The method of claim 23 further comprising:
providing an electric potential well disposed between the first end and the second end of the chamber, the providing comprising reversibly shorting a first electrode to a second electrode; and
temporarily removing the short to allow at least some of the ions to migrate past the first and second electrode toward the second end of the chamber.

27. A method of generating ions in a sample comprising:
providing a sample comprising molecules in a first solvent;
providing a passage through an applied voltage; and
introducing the sample into a second solvent in which the first solvent is partially soluble, the introducing comprising passing the sample through the passage to produce ions from the molecules, the ions being at least partially desolvated with respect to the first solvent.

28. The method of claim 27 wherein the first solvent is polar.

29. The method of claim 27 wherein the first solvent is water.

30. The method of claim 27 wherein the second solvent is non-polar.

31. The method of claim 27 wherein the second solvent is polar.

32. The method of claim 27 wherein the second solvent is substantially free of electrolytes.

33. The method of claim 27 wherein an electric field is present within the second solvent during the introducing.

34. The method of claim 27 wherein the passage is a capillary tube having the applied voltage.

35. The method of claim 27 wherein the passage is a needle having the applied voltage.

36. The method of claim 27 wherein the passage is an inlet having an electrode disposed therein.

37. The method of claim 27 wherein the passages comprises an inlet which passes through a charged plate.

* * * * *

UNITED STATES PATENT AND TRADEMARK OFFICE
CERTIFICATE OF CORRECTION

| | |
|---|---|
| PATENT NO. | : 7,071,465 B2 |
| APPLICATION NO. | : 10/966325 |
| DATED | : July 4, 2006 |
| INVENTOR(S) | : Hill, Jr. et al. |

It is certified that error appears in the above-identified patent and that said Letters Patent is hereby corrected as shown below:

Column 1, Line 8 – Insert --CONTRACTUAL ORIGIN OF THE INVENTION--.

Column 6, Line 36 – Replace "in which ions" with --in which on--.

Column 5, Line 59 – Replace "a, component" with --a component--.

Column 8, Line 13 – Replace "instances, can achieve" with --instances, achieve--.

Column 9, Line 7 – Replace "theoretical based" with --theoretically based--.

Column 10, Line 22 – Replace "19. A" with --19. An--.

Column 11, Line 14 – Replace "can be provide" with --can be provided--.

Column 11, Line 30 – Replace "electrically pulse" with --electrical pulse--.

Column 14, Line 18 – Replace "µl/min" with --µL/min--.

Column 15, Line 30 – Replace "gale" with --gate--.

Column 16, Line 15 – Replace "associate with" with --associated with--.

Column 18, Line 19 – Replace "the passages" with --the passage--.

Signed and Sealed this

Twenty-fourth Day of April, 2007

JON W. DUDAS
*Director of the United States Patent and Trademark Office*